US005902285A

United States Patent [19]

Kudsk et al.

[11] Patent Number: 5,902,285

[45] Date of Patent: May 11, 1999

[54] JEJUNAL FEEDING TUBE

[75] Inventors: Kenneth A. Kudsk, Memphis, Tenn.; Lester D. Michels, Eden Prairie, Minn.

[73] Assignee: Novartis Nutrition AG, Basel, Switzerland

[21] Appl. No.: 08/787,749

[22] Filed: Jan. 27, 1997

[51] Int. Cl.[6] .................................................... A61M 31/00

[52] U.S. Cl. ............................................ 604/270; 604/280

[58] Field of Search ............................ 604/54, 264, 280, 604/270

[56] References Cited

U.S. PATENT DOCUMENTS

| | | | |
|---|---|---|---|
| D. 328,787 | 8/1992 | Picha et al. | D24/108 |
| 4,490,143 | 12/1984 | Quinn et al. | 604/270 |
| 4,613,323 | 9/1986 | Norton et al. | 604/43 |
| 4,668,225 | 5/1987 | Russo et al. | 604/270 |
| 4,769,014 | 9/1988 | Russo | 604/270 |
| 4,781,704 | 11/1988 | Potter | 604/270 |
| 4,795,430 | 1/1989 | Quinn et al. | 604/97 |
| 4,798,592 | 1/1989 | Parks | 604/49 |
| 4,826,481 | 5/1989 | Sacks et al. | 604/54 |
| 4,850,983 | 7/1989 | Brenneman et al. | 604/270 |
| 4,981,471 | 1/1991 | Quinn et al. | 604/97 |
| 5,037,387 | 8/1991 | Quinn et al. | 604/51 |
| 5,057,091 | 10/1991 | Anderson | 604/270 |
| 5,073,166 | 12/1991 | Parks wt al. | 604/93 |
| 5,074,846 | 12/1991 | Clegg et al. | 604/164 |
| 5,080,650 | 1/1992 | Hirsch | 604/97 |
| 5,084,014 | 1/1992 | Picha et al. | 604/54 |
| 5,098,378 | 3/1992 | Piontek et al. | 604/49 |
| 5,100,384 | 3/1992 | McBrian | 604/99 |
| 5,112,310 | 5/1992 | Grobe | 604/175 |
| 5,139,486 | 8/1992 | Moss | 604/164 |
| 5,151,086 | 9/1992 | Duh et al. | 604/51 |
| 5,152,756 | 10/1992 | Quinn et al. | 604/270 |
| 5,167,627 | 12/1992 | Clegg et al. | 604/101 |
| 5,259,367 | 11/1993 | Kirby et al. | 128/8 |
| 5,356,391 | 10/1994 | Stewart | 604/175 |

*Primary Examiner*—Wynn Wood Coggins
*Assistant Examiner*—Deborah Blyveis
*Attorney, Agent, or Firm*—Michael P. Morris

[57] ABSTRACT

The present invention comprises an improved jejunal feeding tube comprising semi rigid tubing attached to the distal end of a percutaneous endoscopic feeding tube. The tubing further contains equidistantly spaced bushing grips on the jejunal feeding tube for ease of placement and securing the jejunal feeding tube to the small intestine.

9 Claims, 2 Drawing Sheets

JEJUNAL FEEDING TUBE

FIELD OF THE INVENTION

The present invention relates generally to enternal feeding methods and devices used in conjunction therein. More specifically, the present invention relates to jejunal feeding tubes and improved configurations thereof for the proper placement of the distal or lower portion of the tube within the lining of the small intestine and its securement thereto.

BACKGROUND OF THE INVENTION

There are many patients affected with disease or other physiological conditions that for one reason or another are unable to receive nutrition normally through the mouth which is then swallowed and broken down and absorbed by the digestive system. People suffering from stroke, Alzheimer's disease, cancer, inflammation or other infirmities, often cannot properly chew or swallow their food or medication which must then be delivered to the patient in another fashion if starvation and malnutrition are to be avoided.

Gastroenterologic feeding tubes have been known for years and are inserted into the stomach by any one of a number of different methods. Generally, a catheter is placed in the body by way of the mouth and using suture thread, is pulled downward into the stomach and either left there or is pushed further down into the jejunum of the small intestine. The feeding tubes may also enter the body either by way of the nasal passageway or by means of a gastrostomy.

In a gastrostomy, a surgical procedure is performed on the abdomen wherein the opening is cut through the skin, facia and stomach wall. A tube is inserted through the opening so as to allow food to be provided directly to the stomach or intestines.

Recently, percutaneous endoscopic gastrostomy (PEG) was developed which makes placement of the enteral feeding tube within the stomach or small intestine a great deal easier. Here, an endoscope is used to visualize the desired insertion site on the gastric mucosa and the subsequent creation of a surgical opening into the stomach through the abdominal wall. The percutaneous endoscopic techniques used to place enteral feeding tubes within the patient are generally carried out in one of three ways.

In a conventional "pull" procedure, an endoscope is inserted through the esophagus of the patient, and the stomach is then inflated. Using the endoscope to locate an appropriate site in the stomach wall, a cannula or needle is then inserted through the stomach wall, and a string inserted through the needle. The needle may then be removed. The string is grasped by means of a snare passing through the endoscope, and the endoscope and snare are pulled up through the esophagus, such that one end of the string comes out through the mouth, leaving the other end protruding through the opening made by the needle. A gastrostomy catheter is then tied to the end of the string which protrudes from the mouth, conventionally by means of another string attached at one end of the gastrostomy catheter.

The catheter is then pulled down into the stomach by pulling on the end of the string which protrudes through the opening in the stomach and the catheter is pulled through the opening as well. The catheter is usually provided with a tapered dilator at the leading end to assist in passing through the stomach wall. The catheter is held in place by a retention means against the interior of the abdominal wall. Another retention means is placed on the exterior, so as to hold the catheter in place against the stomach. The endoscope is reinserted to ensure proper placement of the catheter.

In the technique set forth by Russell, sometimes referred to as the "push" technique, a needle is first inserted into the stomach (at a site located by endoscopy, as with the pull procedure), and then a guide wire is inserted through a lumen in the needle. A small incision is then made in the fascia next to the guide wire, after which an interiorly lubricated sheath having a splittable seam is guided, along with a tapered dilator, over the guide wire and into the stomach. Once the sheath is in place, the dilator and guide wire are removed, and a balloon catheter is inserted through the lubricated central lumen of the sheath. A distal balloon of the catheter is then inflated and the sheath is peeled or split away along its seam or seams, thus leaving the catheter emplaced in the stomach. Sutures are provided to maintain tension of the balloon against the peritoneum.

When the enteral feeding tubes are to be placed in the jejunum or small intestine, generally some additional steps are required. After the enteral feeding tube has been placed through the ostomy and into the stomach, the loop of the suture aids in the proper positioning of the distal end of the feeding tube within portions of the gastrointestinal tract beyond the pylorus valve. Generally, the loop is grasped by endoscopic forceps. By manipulation of the forceps, the loop and the distal end of the enteral feeding tube are properly positioned within either the duodenum or the jejunum.

There are, however, certain drawbacks to this prior art, loop-containing attachment. First, the suture is intended to lead and extend in a forward direction from the distal end of the enteral feeding tube. The suture is, however, made of a non-rigid fabric. For this reason, as the enteral feeding tube is inserted through the PEG tube, or cannula within the ostomy, the suture has a tendency to trail the feeding tube. This tendency causes the suture to become reversed, and to "double-over" the sides of the feeding tube. The suture thus becomes lodged between the enteral feeding tube and the PEG tube, this "doubling over" of the suture inhibits the free movement of the enteral feeding tube through the PEG tube.

Yet another problem arises when the feeding tube has been inserted within the body of the patient. As discussed above, the loop of the suture is grasped by a pair of endoscopic forceps. As it is moved through the body, the suture loop tends to become wetted by and absorbs various body fluids. When the enteral feeding tube is properly positioned within the duodenum or jejunum and the endoscopic forceps are opened to release the wetted suture, that suture may nevertheless stick to the forceps. As a result, the suture and the enteral feeding tube to which it is attached may follow the forceps while the forceps are being withdrawn from the body cavity. In this manner, the enteral feeding tube may be moved from its intended position.

In a third technique which essentially is a surgical one, the tip of the enteral feeding tube is placed in the stomach and is grasped by a forceps or wire loop. In this manner, the tip of the tube is manipulated surgically through the ostomy and is directed from the stomach through the pylorus and into a position within the jejunum which comprises the upper third of the small intestine. However, since the feeding portion of the tube is of relatively small diameter and made of smooth plastic, there is often a great deal of difficulty encountered in grasping, moving, directing and holding the tip of the feeding tube while it is within the lubricous and slippery walls of the gastrointestinal environment. It would therefore be advantageous to provide a means that allows for a better hold of the tube without providing additional objectionable protrusions that might irritate, damage or tear the soft mucosal linings of the esophagus, stomach and small intestine during gastrointestinal implantation.

U.S. Pat. No. 5,098,378 to Piontek et al. discloses and claims a replacement gastrostomy tube for jejunal feeding in which an expandable component of the tube is located at the distal end thereof. Fluid is passed through a fluid flow channel which enters the expandable component and inflates it like a balloon. In this fashion, the balloon and an adjacent retention device are pressed against the wall of the stomach, securing the feeding tube in the stoma.

U.S. Pat. No. 5,152,756 to Quinn et al. discloses an improved enteral feeding tube in which a bulbous extension member is attached to the distal end of the feeding tube. The extension is comprised of a stem portion that projects beyond the end of the tube parallel to the axis of the tube and forms a large spherical tip at its end. In this manner, the stem extension can be more easily grasped by forceps for surgical placement.

U.S. Pat. No. 5,100,384 to McBrian et al. discloses a device for percutaneous intubation in which the feeding tube comprises an inflatable lumen that expands as a water swellable foam material contained therein absorbs water from the gastrointestinal cavity after intubation. A wire or suture loop is disposed at the terminal end of the feeding tube lumen for attachment to a wire used in pulling the tube through the esophagus and stomach during the intubation procedure.

U.S. Pat. No. 5,037,387 also to Quinn et al. discloses a method for positioning an enteral feeding tube within a patient's body and a tube for use therein comprising a flexible polyurethane tube and a rigid stem portion at the distal end thereof that forms an outlet from which the nutritional fluid flows. The stem itself ends in a spherical tip or ring which prevents the possibility of a puncture of the gastrointestinal tract as the enteral feeding tube is pulled.

None of these prior art gastrostomy tubes provide an easy and effective means to enable the surgeon to quickly and safely place the tube within the jejunum. Moreover, none of the prior art methods or devices allow the surgeon to safely locate and grasp the distal end of the feeding tube without posing a risk of injury to the organ walls and fascia. Nothing suggests a means whereby despite the slippery and lubricous environment of the gastrointestinal tract, the tube can be firmly grasped and directed into the jejunum without the risk of getting caught or lodged within the pyloric valve or duodenum.

SUMMARY OF THE INVENTION

The present invention is an improved jejunal feeding tube wherein a number of bushing grips are dispersed along the length of the tube. In this manner, the surgeon can grasp the tube through an ostomy and this enables the surgeon to easily place the distal end of the tube within the jejunum. The grips are designed with tapered, conical tips so there is little risk of clogging the jejunum or causing other injury to the walls of the gastrointestinal cavity.

DETAILED DESCRIPTION OF THE INVENTION

Jejunal feeding tubes are primarily useful in enteral feeding situations where the patient suffers from gastric reflux. In reflux, digested gastric residue is refluxed or vomited up the esophagus. This may often result in asphyxiation and death for bed-ridden patients and those who cannot swallow voluntarily. This problem can be directly attributable to the presence of the gastrostomy tube to begin with. A jejunal feeding tube on the other hand passes through the stomach and the pylorus and then enters the small bowel of the duodenum and the jejunum.

Figure 1:
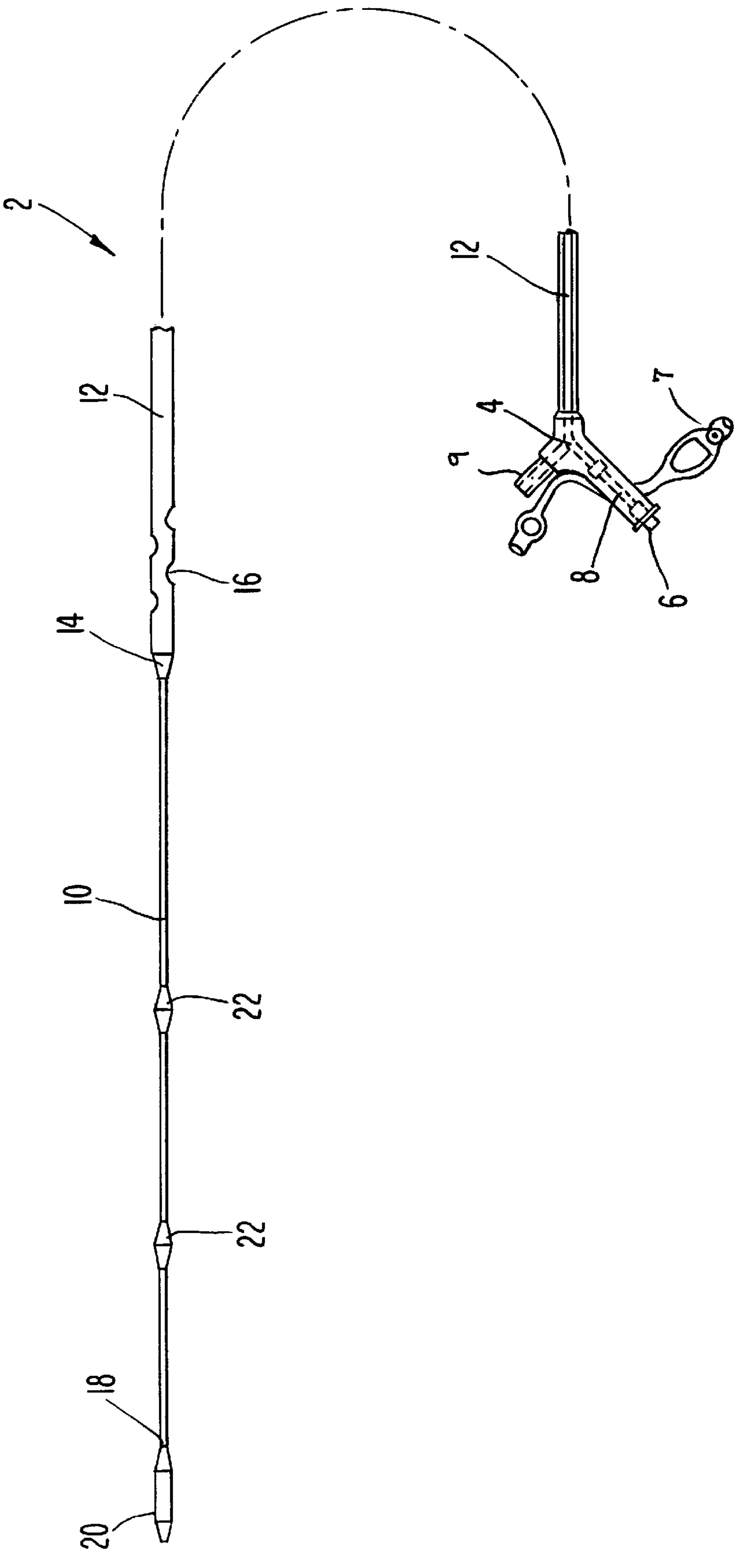
FIG. 1 is an overall view of the jejunal feeding tube placement device of the present invention.

Referring now to FIG. 1, one embodiment of the surgically placed jejunal feeding tube (2) is presented in order to give a better understanding of the present invention. The jejunal feeding tube (2) is comprised of a manifold connector (4) and a second connector or feed port (6) which essentially make up the entry port for delivery of the enteral composition and medication as well as the exit port for gastric drainage.

Either port may be useful in the delivery of medication, of enteral compositions or the drainage of intestinal contents. The feed port (6) may have placed within it a stylet (8) which serves to temporarily provide additional stiffness to the tube during positioning of the tube in a patient's gastrointestinal tract and may be removed thereafter. The feed port is contiguous with the smaller bore tubing (10) which extends the full length of the tube and comprises the jejunal tube while the manifold/connector is contiguous with the larger bore outer tubing (12) which terminates at a tapered sleeve (14) some distance from the end of the tube and comprises the gastric tube. Both the small and large bore tubing may be made of flexible material such as polyurethane so as to allow for easy manipulation of the device during its implantation and removal.

The gastric tube also contains holes (16) near its distal terminus which are useful as conduits of gastric fluid into the tube to be drained from the manifold/connector.

Figure 2:
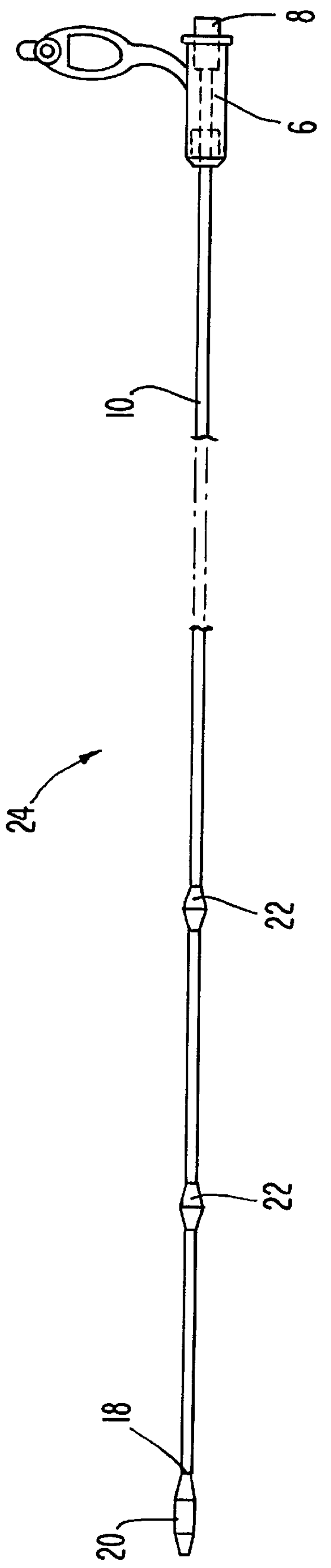
FIG. 2 is an overall view of a single tube embodiment of the jejunal tube placement device of the present invention.

At the tip or distal end of the jejunal feeding tube position (18) is a bolus (20) for the actual discharge of the nutritional supplement or medicine to the jejunum for absorption therein. The bolus (20) is essentially an oblong piece of rubber or plastic such that foods passing through the tubing exit the system through the tip into the jejunum. The feeding tube also contains at least one and preferably two or three bushing grips (22) spaced equidistantly from the bolus tip (20) and each other. The bushing grips are essentially tapered, barrel-shaped protrusions surrounding the jejunal feeding tube (10). As can be seen in FIG. 1, the ends of each grip (22) are approximately the same diameter and circumference as the tube (10). Each grip is flared however, towards the center so that the circumference and diameter of each grip at the center is greater than that of the tube (10). This ensures that as the jejunal tube (10) is pushed and/or pulled as it is passing through the esophagus, stomach and jejunum for placement, the least amount of resistance is afforded by the tapered sides of the grips in both directions. The tapered form reduces the chances of tissue traumatization and enhances the ease of tube placement. Referring now to FIG. 2, a second embodiment of the surgically placed jejunal feeding tube (24) is presented to understand a single tube version of the device wherein only the smaller bore tubing (10) and feed port (6) with assembled stylet (8) comprise the major portions of the tube. The same bolus (20) at the distal end of the tubing (18) and bushing grips (22) are present on the tubing in the positions and for the purposes described above. This device is useful when there is need for delivery to or drainage of fluid in only the intestine.

The jejunal feeding tube (10) enters the stomach and lower intestines by way of a previously inserted PEG tube which contains the jejunal tubing (10) from the stylet bolus grip (20) to the manifold (4) of the dual port stylet (6). In this way, the jejunal placement tube is inseparable from the PEG tube.

The jejunal feeding tube of the present invention is more specifically a nasojejunal feeding tube for intraoperative placement as part of a laparotomy. The tube itself is inserted into the stomach through the nasopharyngeal passageway. Once this distal portion is in the stomach, the tip is manually grasped by way of an ostomy and the tip is then guided past the pylorus into the duodenum by manually grasping and pushing it. The stylet bolus (20) and bushing grips (22) facilitate this movement and insure the tube can be easily manipulated and advanced through the small bowel and the tip and bushing grips may be used to advance the tube further, into the intestine. Optimal positioning locates the tip of the tube at the ligament of Triest.

Once the distal end of the tube is properly placed, the stylet (20) within the tube is surgically removed and upon fluoroscopic or x-ray confirmation that the tube is properly placed within the jejunum, feeding can begin immediately. Fluoroscopic replacement of the nasojejunal tube may also be easily conducted using guidewire exchange. When jejunal feeding is no longer necessary, the bushing grips (22) of the present invention allow for a firmer, easier retention and retrieval of the tube.

Again, referring now to FIG. 2, a second embodiment of the feeding tube is shown consisting of a single entry port for the delivery of nutritional formula to the system. As before, the opening can be plugged using the attached rubber stopcap (7) when no formula is being administered. The tapered bushing grips (22), the terminal stylet bolus (20) and feeding tube (10) are integral with the flexible PVC tubing (10) as before.

It is recognized that similar modifications can be made to jejunal feeding tubes in order to aid the grasping and retention process that are not specifically set forth herein. To the extent that any such variations do not materially change the design and/or function of the tubes as described, they are considered to be within the spirit and scope of the invention as defined in the claims that follow.

What is claimed is:

1. An improved jejunal feeding tube for the nutritional or medicinal treatment of a patient, said feeding tube comprising an enteral feeding port, flexible tubing in open communication therewith; a stylet bolus located proximate to an end of said feeding tube, and located distally with respect to said feeding port, and multiple bushing grips, all of which are equidistantly spaced, along with said stylet bolus, along said tube for aiding in the movement and placement of said tube.

2. The jejunal feeding tube of claim 1 wherein said stylet bolus extends about the periphery of the distal end of said tube.

3. The jejunal feeding tube of claim 2 wherein said bushing grips are tapered.

4. The jejunal feeding tube of claim 3 wherein said bushing grips are tapered at both ends.

5. The feeding tube of claim 4 wherein said tube is integral with a more flexible portion of plastic tubing.

6. The jejunal feeding tube of claim 5 wherein said flexible tubing connects to a multiple outlet feeding port for the administration of nutritional formula or medication at the end opposite the distally located stylet bolus of said jejunal feeding tube.

7. The jejunal feeding tube of claim 6 wherein said bushing grips aid in the retention and placement of the tube beyond the pylorus and into the duodenum of the small intestine.

8. A method for the insertion and placement of a jejunal feeding tube using the device of claim 1.

9. The method of claim 8 wherein said jejunal feeding tube is inserted into a patient's body through a percutaneous endoscopic gastrostomy (PEG) tube.

* * * * *